United States Patent [19]

Ngo et al.

[11] Patent Number: 5,082,929
[45] Date of Patent: Jan. 21, 1992

[54] IMMOBILIZATION OF GLYCOCOMPOUNDS AND GLYCOCONJUGATES

[75] Inventors: That T. Ngo, Irvine; Gilbert Fung, Valinda, both of Calif.

[73] Assignee: BioProbe International, Inc., Tustin, Calif.

[21] Appl. No.: 564,908

[22] Filed: Aug. 8, 1990

[51] Int. Cl.$^5$ .................... C07K 17/14; C12N 11/14
[52] U.S. Cl. .................... 530/391; 435/174; 436/527; 436/532; 525/54.1
[58] Field of Search ............ 530/391; 435/174; 436/527, 532; 525/54.1

[56] References Cited

U.S. PATENT DOCUMENTS

| | | | |
|---|---|---|---|
| 4,419,444 | 12/1983 | Quash | 435/7 |
| 4,801,687 | 1/1989 | Ngo | 530/387 |
| 4,874,813 | 10/1989 | O'Shannessy | 525/54.1 |
| 4,948,836 | 8/1990 | Solomon et al. | 525/54.1 |

FOREIGN PATENT DOCUMENTS 88695 9/1983 European Pat. Off. .

OTHER PUBLICATIONS

O'Shannessy et al. (1990), Anal. Biochem. 191:1-8.
Cress et al. (1989), Am. Biotech. Lab. 7(2):16-19.
Pierce, Immunotechnology Catalog, pp. B10, Product No. 44900B (1990).

Primary Examiner—John Doll
Assistant Examiner—Kay Kim
Attorney, Agent, or Firm—Nilsson, Robbins, Dalgarn, Berliner, Carson & Wurst

[57] ABSTRACT

A method for attachment of glycocompounds and glycoconjugates to hydrazide gels, wherein a solution of glycocompound or glycoconjugate containing a suitable oxidizing agent is brought into contact with the hydrazide gel without prior removal of the oxidizing agent. Suitably, the solution is introduced into a cartridge containing the hydrazide gel. In accordance with a first embodiment, this method requires relatively short incubations of about 30 minutes for oxidation of the glycosaccharide moiety of the glycocompound or glycoconjugate, followed by about 15 minutes for binding the oxidized glycocompound or glycoconjugate to the hydrazide gel. Pursuant to another embodiment, incubation with the oxidizing agent is carried out simultaneously with bringing the solution into contact with the gel (e.g., within the cartridge). Synthetic polymer gels with terminal hydrazide groups are particularly suitable for use in this method, as these gels are especially resistant to oxidizing agents such as sodium periodate.

16 Claims, 2 Drawing Sheets

IMMOBILIZATION OF GLYCOCOMPOUNDS AND GLYCOCONJUGATES

BACKGROUND OF THE INVENTION

The invention relates to methods for immobilization of glycocompounds and glycoconjugates, and in particular immunoglobulins, onto solid supports for use in affinity chromatography.

Affinity chromatography is a well-established technique used to purify a variety of materials of biological and chemical interest, for example proteins. The system relies on the unique interaction between an immobilized affinity ligand and the molecule of interest. Since the introduction of affinity chromatography methods, immobilized ligands on solid supports have found application in the purification of receptors, enzymes and antibodies. Immobilized antibodies and binding proteins have also been used as biosensors and in bioreactors. In view of the particular importance of immunoglobulins in research, diagnostic procedures and bioseparations, much of the work in this field has focused on methods for binding antibodies; while the following discussion relates in particular to immunoglobulins, it should be understood that many of the principles involved are of more general applicability to a wide class of potential ligands.

Most of the published reports relating to the immobilization of ligands, such as in particular antibodies, have emphasized the central importance of the stability and retention of specific binding characteristics of the immobilized species. To this end, a great deal of research into the chemistry of binding has taken place and a variety of activated supports are now commercially available. Antibodies have been bound to a variety of solid supports, including matrices prepared for covalent binding by CNBr activation [Cuatrecasas, P., "Protein Purification by Affinity Chromatography," J. Biol. Chem. 245, 3059-3065 (1970)] or periodate activation [Ferrua, B., et al., "Coupling of Gamma-globulin to Microcrystalline Cellulose by Periodate Oxidation," J. Immunol. Methods. 25, 49-53 (1979)], and matrices containing N-hydroxysuccinimide esters [Laporte, D. C., et al., "Inhibition of Escherichia Coli Growth and Respiration by Polymyxin B Covalently Attached to Agarose Beads," Biochemistry 16, 1642-1648 (1977); Wilchek, M. et al., "Limitations of N-Hydroxysuccinimide Esters in Affinity Chromatography and Protein Immobilization," Biochemistry 26, 2155-2161 (1987)].

Generally, the established procedures covalently couple antibodies to solid supports through the reactive amino group of an amino acid residue. Previously, the use of various solid phase supports for antibody immobilization has been reported [Little, M. C., et al., "Enhanced Antigen Binding to IgG Molecules Immobilized to a Chromatographic Support via Their Fc Domains," BioChromatography 3, 156-159 (1988); Matson, R. S., and M. C. Little, "Strategy for the Immobilization of Monoclonal Antibodies on Solid Phase Supports," J. Chromatogr. 458, 67-77 (1988)].

However, this method of binding biological materials via amino acid residues has several inherent problems. For instance, if lysine groups are present on the surface of the antibody molecule, multi-site attachment frequently occurs and the antibody may lose activity. In addition, multiple orientations of the antibody on the gel surface are possible, depending on how many and which lysine groups bind to the gel.

Moreover, because of the lack of specificity in the binding reaction when coupling occurs through the reactive amino groups of amino acid residues, the antibody may be bound at a site within, or in close proximity to, a ligand binding site. This further reduces the specific binding activity of the ligand.

Many proteins that could be bound to solid supports for use in affinity techniques are glycoproteins. The oligosaccharide moieties of these glycoproteins are usually located at sites away from the ligand binding site and are not believed to be involved in the binding of bioactive molecules [O'Shannessy D. J., and R. H. Quarles, "Labeling of the Oligosaccharide Moieties of Immunoglobulins," J. Immunol. Methods 99, 153-161 (1987); Williams, D. G., "Comparison of Three Conjugation Procedures for the Formation of Tracers for Use in Enzyme Immunoassays," J. Immunol. Methods 72, 261-268 (1984); Tsang, V. C. M., et al., "Quantitative Capacities of Glutaraldehyde and Sodium m-Periodate Coupled Peroxidase-Anti-Human IgG Conjugates in Enzyme-Linked Immunoassays," J. Immunol. Methods. 70, 91-100 (1984)]. Therefore, the oligosaccharide moieties of these glycoproteins may be specifically modified with little or no effect on the ligand binding properties of the glycoproteins.

A particularly advantageous technique for immobilization of glycocompounds and glycoconjugates, and in particular glycoproteins such as immunoglobulins, involves the modification of the oligosaccharide moieties so as to introduce therein suitable reactive groups for formation of covalent bonds with complementary reactive groups on a matrix material. Thus, for example, hydrazide groups (which react with aldehydes resulting from the oxidation of the oligosaccharide moieties of glycoconjugates) have been successfully exploited for the preparation of immunoglobulins bound to a solid support [O'Shannessy, D. J. and Hoffman, W. L., "Site-Directed Immobilization of Glycoproteins on Hydrazide-Containing Solid Supports," Biotechnol. & Appl. Biochem. 9, 488-496 (1987); Hoffman, W. L. and O'Shannessy, D. J., "Site-specific Immobilization of Antibodies by their Oligosaccharide Moieties to New Hydrazide Derivatized Solid Supports," J. Immunological Methods 112, 113-120 (1988); Turkova, J. et al., "Carbohydrates as a Tool for Oriented Immobilization of Antigens and Antibodies," J. Chromatography 500, 585-593 (1990)].

More recently, the performance of hydrazide AvidGel TM Ax (BioProbe International) as a support matrix for immobilization of IgG for use in affinity chromatography has been examined [Cress, M. and T. Ngo, "Site Specific Immobilization of Immunoglobulins," American Biotech. Lab. 7, No. 2 16-19 (1989)]. It was demonstrated that rabbit anti-human IgG retained higher biological activity after binding to a hydrazide-containing solid support using AvidGel TM Ax.

Nonetheless, prior art methods exploiting the binding of immunoglobulins via their oligosaccharide moieties to hydrazide gels have heretofore required a relatively time-consuming and complicated procedure in which oxidation of the oligosaccharide moieties (typically, using sodium periodate) is invariably followed immediately by a separate process step for removal of unreacted periodate and any aldehydes released from the carbohydrate side chains. This separation procedure (typically, effected by column chromatography or dialysis) not only substantially increases the amount of time necessary to complete the binding procedure and greatly dilutes the sample, but may also reduce significantly the amount of valuable antibody recovered for binding. As the presence of any sodium periodate was considered to adversely effect the binding procedure, the conventional wisdom has been not to collect and pool fractions other than the protein peak, notwithstanding the potential loss and dilution of valuable antibodies in those peaks [see. e.g., Bio-Rad, "Affi-Gel ® Hz Immunoaffinity Kit Instruction Manual, Catalog Number 153-6060, p. 5 (1987)].

In addition, it is highly desirable to effect the binding process as quickly as possible to reduce the amount of time during which immunoglobulins in an impure fraction may be subjected to protease and oxidative attack. The known methods for separation of sodium periodate from oxidized IgG using desalting gel column chromatography or dialysis are time-consuming and cause substantial dilution and/or loss of the sample. As a consequence, even after the recommended column chromatography it is generally necessary to perform sample concentration steps, which of course increase the processing time and the risk of denaturing the proteins and further loss of the sample.

It would be advantageous to provide a method for binding oxidized glycocompounds and glycoconjugates, and in particular glycoproteins such as valuable immunoglobulins, which could be carried out as rapidly as possible and in the least number of separate steps.

It is therefore an object of the present invention to provide a method for the binding of oxidized glycocompounds and glycoconjugates, and in particular glycoproteins, to hydrazide gels while obviating the problems inherent in the prior art methods.

SUMMARY OF THE INVENTION

In accordance with the present invention, hydrazide gels may be used to quickly and efficiently couple oxidized glycocompounds and glycoconjugates (hereinafter, "glycoconjugates"), and in particular glycoproteins such as antibodies, from a variety of sources without prior removal of oxidizing agent (e.g., sodium periodate) from the oxidation mixture. In accordance with a preferred embodiment of the invention, the hydrazide gel is conveniently supplied in the form of a cartridge. This method thus eliminates entirely the time-consuming dialysis, desalting and/or concentration steps heretofore required for preparation of bound glycoconjugates. The coupled glycoconjugate cartridge can then be directly used, e.g., to purify materials of interest (for example, specific antigens in the case of bound antibodies). This method is fast and simple, and the only equipment necessary to use such a cartridge is a syringe. The quick processing reduces the potential loss of activity that can occur by maintaining glycoconjugates (such as immunoglobulins) for long periods of time in an unpurified form, in which they are particularly subject to protease and/or chemical attack.

DETAILED DESCRIPTION OF THE INVENTION

Figure 1:
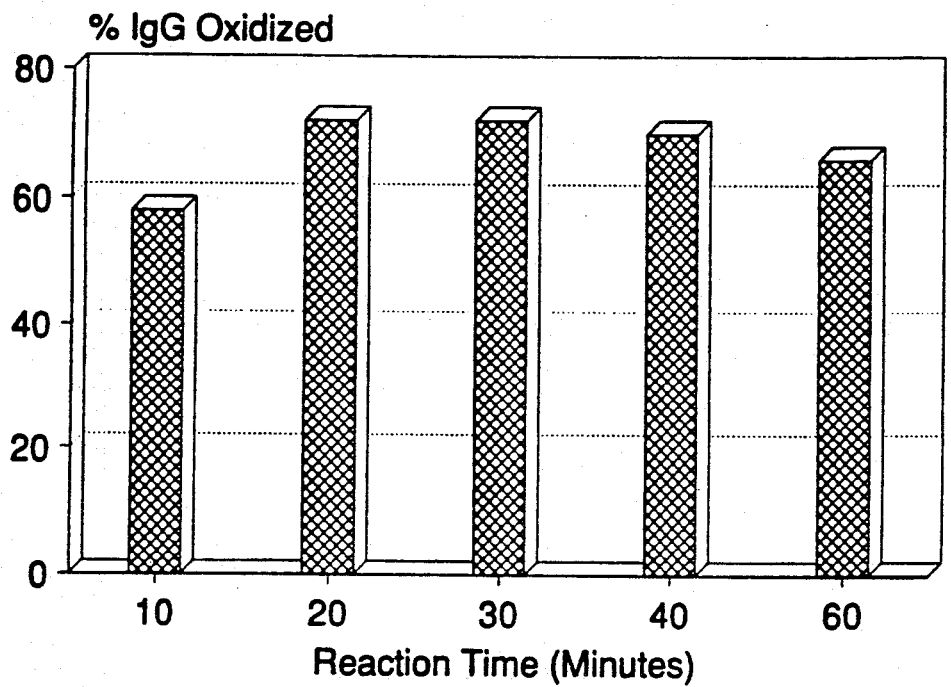
FIG. 1 illustrates the time course of IgG oxidation with sodium periodate.

In accordance with the present invention, the rapid and efficient site-directed immobilization of glycoconjugates, and in particular immunoglobulins, onto a hydrazide gel is effected by bringing an oxidized glycoconjugate in a solution containing the oxidizing agent (e.g., sodium periodate or an enzymatic oxidizing system) into contact with the hydrazide gel without prior removal of the oxidizing agent. It was determined that when using the preferred hydrazide gels described herein, the presence of sodium periodate in the oxidized IgG solution does not have a detrimental effect either on the binding of IgG to the gel, or on the properties of the gel itself.

Particularly advantageous for use in accordance with the present invention is an AvidChrom cartridge, containing Hydrazide AVIDGEL ™ F (a vinyl alcohol polymer composed exclusively of C, H and O atoms and containing terminal hydrazide groups) as obtained from BioProbe International (Tustin, Calif.). Hydrazide AVIDGEL ™ is a polymer of N-acryloyl-2-amino-2-hydroxymethyl-1,3-propanediol that has free hydrazide groups. Hydrazide AvidGel ™ F has several advantages over other hydrazide derivatized solid supports, such as agarose. Hydrazide AvidGel ™ is pressure resistant up to 100 psi, allowing for faster flow rates. The matrix is also resistant to periodate oxidation. The latter advantage make it easy to couple periodate-oxidized glycocompounds and glycoconjugates (e.g., antibodies) without the need for any separate desalting step as heretofore required in prior art methods. Other hydrazide gels resistant to specific oxidizing agents commonly employed may also be used in accordance with the present invention; for example, HiPAC ™ Hydrazine Activated Column material (made from silica based material) available from Chromatochem, Inc., Missoula, Mont. and AFFI-PREP ® HZ Polymeric Support (an acrylate polymer composed exclusively of C, H and O atoms available from Bio-Rad, Richmond, Calif. are both resistant to sodium periodate.

In using the preferred hydrazide gel cartridges, the only equipment necessary to carry out the inventive method is a syringe. The glycoconjugate is injected directly into the cartridge in a solution containing the oxidizing agent without any purification step whatsoever. After a short incubation, the glycoconjugate is immobilized onto the solid support and the hydrazide cartridge is ready for further use.

It has been determined in general that only a 30 minute incubation with sodium periodate prior to injection of the solution into the cartridge is sufficient for IgG oxidation. Similarly, a 15 minute incubation inside the cartridge has been found to be sufficient for immobilization of oxidized human IgG.

In accordance with a further embodiment of the present invention, it is also possible to perform both the oxidation and the immobilization of the glycoconjugate in a single step within the hydrazide cartridge. Pursuant to this method, a solution of the glycoconjugate and oxidizing agent is introduced into the cartridge and maintained therein for a predetermined incubation period. Following incubation, one or more washing buffers is introduced into the cartridge; unbound oxidized glycoconjugate, unoxidized glycoconjugate and the oxidizing agent are thereby removed from the cartridge. Using human IgG, it was determined that optimum results may be achieved after only about 30 minutes. By repeating the incubation and washing steps sequentially, it is possible to increase the amount of glycoconjugate bound in accordance with this embodiment of the method, relative to what is achieved in a single incubation/wash cycle.

The hydrazide gel cartridges of the invention may be used to immobilize IgG from various mammalian species at high capacity and efficiency. The coupling rate of glycoprotein and the amount of glycoprotein bound to hydrazide cartridges is dependent on at least two factors: the amount of carbohydrate attached to the antibody; and the accessibility of this carbohydrate to oxidation and coupling to the solid phase ligand. Therefore, each species and class of antibody would be expected to have a different coupling rate within the hydrazide gel cartridge, depending on the degree and type of glycosylation. Nonetheless, it has been determined with a number of different glycoproteins that the inventive procedure may be carried out quickly and efficiently relative to prior art methods.

The immobilized glycoconjugate, such as IgG, remains functional and stable for multiple cycles of absorption and desorption in actual purification runs. Thus, the hydrazide gel cartridge provides a fast, simple and efficient method to immobilize antibody for use in immunoaffinity chromatography, and can also be used to monitor functional antibody production in hybridoma harvest supernatants, ascites or immune serum. It is reliable and reproducible, and the quick processing involved should reduce the loss of activity that can occur by attack of chemical and/or biological agents.

The invention will be better understood by reference to the following examples which are intended for purposes of illustration and are not to be construed as in any way limiting the scope of the present invention, which is defined in the claims appended hereto.

EXAMPLES

Hydrazide AvidGel ™ F was obtained from BioProbe International (Tustin, Calif.). Human and goat immunoglobulins used in this study were purchased from Sigma Chemical Company (St. Louis, Mo.). The IgG fraction of rabbit anti-human IgG (Y chain specific) was purchased from BioSpecific Company (Emeryville, Calif.), and mouse IgG was obtained from Scripps Laboratories (San Diego, Calif.). All other reagents and chemicals were obtained from Sigma Chemical Company, or were of commercially available reagent grade. AvidChrom ™ Hydrazide cartridges were prepared using hydrazide AvidGel ™ F from BioProbe International (Tustin, Calif.).

EXAMPLE 1

Binding of IgG to AvidChrom Hydrazide Gel Following Periodate Oxidation

A solution of 0.05M sodium acetate (pH 4 to pH 7, preferably pH 5) was used as coupling buffer. A solution of 0.1M sodium acetate and 0.5M sodium chloride (pH 3.5) was used as washing buffer. A solution of 0.025M Tris base, 0.15M sodium chloride, and 0.05% sodium azide (pH 7.4) served as storage buffer.

To determine the optimum time required to oxidize IgG, a solution of IgG (3 mg/ml) in coupling buffer was mixed with sodium periodate (10 mM). The reaction mixture was wrapped in aluminum foil and incubated at room temperature. At different time intervals (10, 20, 30, 40, and 60 minutes) aliquots of 1 ml of reaction mixture were directly injected into separate hydrazide gel cartridges which had been equilibrated with coupling buffer. These cartridges can quantitatively couple not less than 10 mg of IgG per ml of gel within 15 minutes. Each cartridge was incubated 15 minutes at room temperature. Subsequently, the cartridges were washed with 5 ml of each of the following buffers: coupling buffer, washing buffer and storage buffer. The unoxidized IgG was determined from the absorbance values at 280 nm of the collected washes.

To determine the optimum time required for the binding of oxidized IgG to the hydrazide cartridge, a solution of IgG (5 mg/ml) in coupling buffer was mixed with sodium periodate (10 mM). The reaction mixture was wrapped in aluminum foil and incubated 30 minutes at room temperature. At the end of the incubation time, aliquots of 1 ml of oxidized IgG were injected into separate hydrazide gel cartridges. The cartridges were incubated at room temperature 5, 15, 30, and 60 minutes. Subsequently, the cartridges were washed with 5 ml each of the following buffers: coupling buffer, washing buffer, and storage buffer. The percent coupling efficiency was calculated as follows:

$$\text{Amount of } IgG = \frac{\text{Abs. at 280 nm}}{1.35} \times (\text{Dilution factor} \times \text{total sample volume})$$

$$\% \text{ } IgG \text{ coupled} = \frac{\text{Total } IgG \text{ before coupling} - \text{total uncoupled}}{\text{Total } IgG \text{ before coupling}}$$

To examine the loading capacity of the hydrazide gel cartridge, human IgG (3 to 17 mg) was dissolved in 1 ml of coupling buffer and incubated with sodium periodate (10 mM) for 30 minutes at room temperature. At the end of the incubation time, between 0.8 and 1 ml of oxidized IgG was directly injected into the hydrazide gel cartridges and incubated for 15 minutes. Subsequently, the cartridges were washed with 5 ml of each of the following buffers: coupling buffer, washing buffer, and storage buffer. The percent coupling efficiency was calculated as previously described.

Table 1 summarizes the binding efficiency of hydrazide gel cartridges for some of the more common antibodies routinely attached to affinity supports. The binding efficiency was 59.4%, 68% and 73% for goat, bovine and mouse, respectively.

TABLE 1

Coupling of Polyclonal Antibodies from Different Species to Hydrazide AvidChrom Cartridge

| Antibody Species | Amount of IgG (mg) | % Antibody Coupled |
|---|---|---|
| Goat | 1.2 | 59.4 |
| Bovine | 2.1 | 68 |
| Mouse | 4.1 | 73 |

To determine the utility and versatility of this method for immobilizing antibodies from different mammalian species, goat (1.2 mg/ml), bovine (2.1 mg/ml) and mouse IgG (4.1 mg/ml) in coupling buffer were incubated 30 minutes with sodium periodate (10 mM) at room temperature. One ml of each of the oxidized antibodies was then injected into the hydrazide gel cartridges. After 15 minutes incubation, the cartridges were washed with 5 ml of the following buffers: coupling buffer, washing buffer, and storage buffer. The percent coupling efficiency was calculated as previously described.

To determine the specific binding capacity and also the functionality of immobilized IgG, 1.3 mg rabbit anti-human IgG (polyclonal) was immobilized on a hydrazide gel cartridge. A solution containing 2.5 mg human IgG in 0.5 ml phosphate buffer saline (PBS) was then injected into the cartridge. The cartridge was incubated for 20 minutes at room temperature. Subsequently, the cartridge was washed with PBS to remove any nonspecifically bound IgG. The bound human IgG was then eluted from the cartridge with 0.1M sodium acetate (pH 3.5) and sodium chloride 0.5M. The amount of IgG in both the elution buffer and PBS wash was determined by measuring the absorbance at 280 nm. The specific binding capacity of the immobilized antibodies may be defined as milligrams of human IgG eluted divided by milligrams of antibody coupled to the gel. In this case, specific binding capacity of 0.31 mg human IgG per rabbit antihuman IgG was obtained. This has been found to be a typical value.

Figure 2:
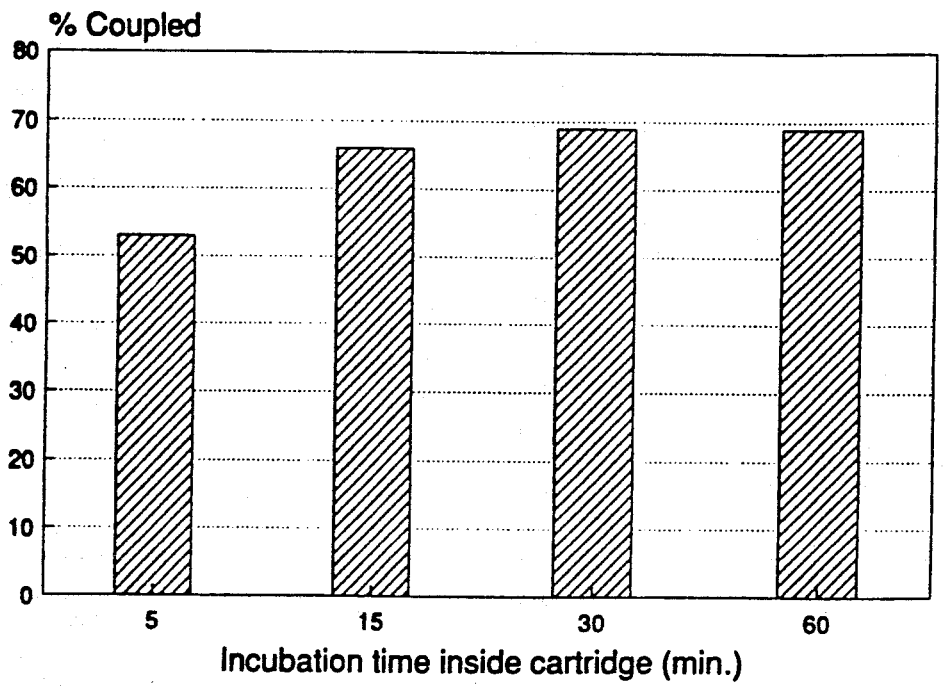
FIG. 2 illustrates the time course of immobilization of oxidized IgG onto a hydrazide gel cartridge.

As illustrated in FIG. 1, a 30 minute incubation of IgG with 10 mM sodium periodate is sufficient for maximum oxidation. As a result, 30 minute incubation with sodium periodate was used for IgG oxidation for subsequent experiments. The time course of immobilization of oxidized IgG to the hydrazide gel cartridge is shown in FIG. 2. There were no significant differences in binding at 15, 30 or 60 minutes. Based on these results, a 15 minute incubation inside the cartridge was chosen as a standard time for immobilization of oxidized human IgG.

Figure 3:
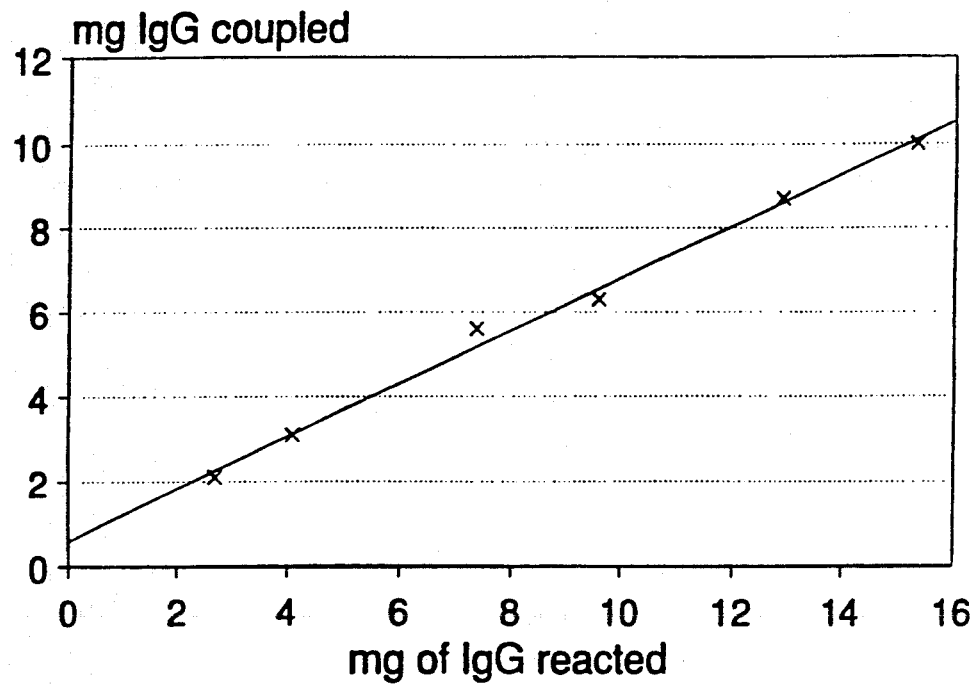
FIG. 3 illustrates the loading course for the immobilization of oxidized human IgG onto a hydrazide cartridge.

The loading course for the immobilization of oxidized human IgG on a hydrazide cartridge is shown in FIG. 3. Hydrazide gel cartridges couple human IgG at a high capacity and efficiency. Applying between 2.6 to 15.5 mg oxidized human IgG gave a yield of 1.8 to 8 mg coupled per one milliliter of gel. This corresponds to a coupling efficiency of between 65 to 80%. Saturating conditions were not achieved with application of up to 15.5 mg IgG/ml of gel.

To determine the specific binding capacity and the reusability of hydrazide gel cartridge-immobilized IgG, rabbit antihuman IgG antibody was immobilized on a hydrazide gel cartridge. The specific binding capacity of the antibody (defined as milligrams of human IgG eluted divided by milligrams of antibody coupled to the gel) was evaluated using human IgG. The specific binding capacity for the hydrazide gel cartridge with 1.3 mg rabbit anti-human IgG immobilized thereto was 0.3 mg of bound human IgG per mg of immobilized anti-human IgG.

Figure 4:
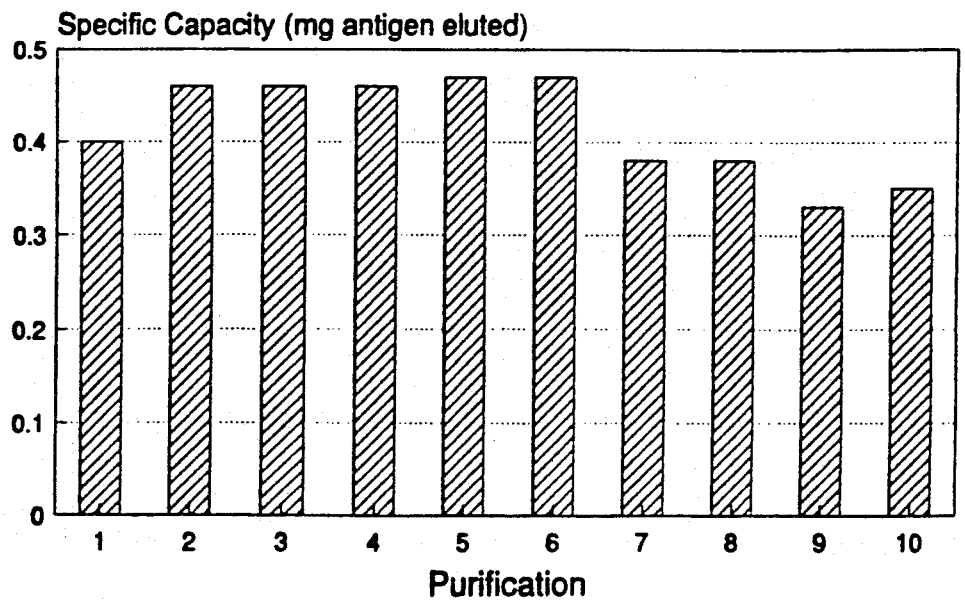
FIG. 4 illustrates the results of repeated cycles of binding and elution using a cartridge in accordance with the present invention in the purification of an antigen.

Immobilized IgG in the cartridge remains stable under common affinity chromatographic conditions, as illustrated in FIG. 4. Human IgG (2.5 mg/ml) was purified using rabbit anti-human IgG (1.3 mg) immobilized on a hydrazide cartridge. Each cycle consisted of equilibrating the cartridge with PBS, loading the sample to be purified, washing with PBS, eluting the IgG with 0.1M sodium acetate and 500 mM sodium chloride (pH 3.5), and a final wash with PBS. The volume and absorbance at 280 nm was measured for each eluted sample, and the mg of antibody isolated was determined as previously described. As is shown in FIG. 4, the hydrazide gel cartridge retained 80% of its original capacity after nine repeated cycles of binding and elution in the purification of an antigen.

EXAMPLE 2

Simultaneous Periodate Oxidation of IgG and Binding to AvidChrom Hydrazide Gel

A solution of 1–3 mg IgG and 10 mM sodium periodate was introduced in 0.33 ml aliquots into a AvidChrom TM Hydrazide cartridge and maintained therein for incubation times of 15, 30, 45 and 60 minutes. Upon completion of the incubation period, the cartridge was washed sequentially with 3–4 ml of 50 mM sodium acetate (pH 5.0), 3–4 ml of 50 mM sodium acetate in 0.5M sodium chloride (pH 3.5), and 5–10 ml of 25 mM TrisHCl (pH 7.0). This washing process caused unbound oxidized IgG and any unoxidized IgG to pass through the cartridge. The amount of glycoconjugate bound was determined by subtracting the amount recovered in the washes from the initial amount introduced into the cartridge.

Using the above method, the optimal time required for efficient immobilization of a glycoconjugate (IgG) in the hydrazide cartridge was determined. The results are summarized in Table 2.

TABLE 2

| Effect of Incubation Time on Amount of Immunoglobulin Bound | |
| --- | --- |
| Incubation Time (min.) | % Immunoglobulin Bound |
| 15 | 50 |
| 30 | 70 |
| 45 | 59 |
| 60 | 53 |

The effects of repetitive cycling of oxidized immunoglobulin G through the hydrazide cartridge were investigated by sequentially repeating the following cycle of steps. First, a 0.3 ml aliquot of a solution of 1–3 mg/ml IgG in 10 mM sodium periodate was injected into the cartridge and incubated therein at room temperature for 30 minutes. Then, the cartridge is washed with 10 ml of 50 mM sodium acetate (pH 5.0), followed by 10 ml of 50 mM sodium acetate in 0.5M sodium chloride (pH 3.5) and 10 ml of 50 mM sodium acetate (pH 5.0). The next cycle begins with another 0.3 ml aliquot of oxidized IgG. As summarized in Table 3, there is an increase in the amount of immunoglobulin bound with the increasing number of cycles completed.

TABLE 3

| Effect of Number of Cycles on Amount of Oxidized Immunoglobulin Bound to Gel in Cartridge | |
| --- | --- |
| Number of Cycles | mg IgG Bound |
| 1 | 1.2 |
| 2 | 3.4 |
| 3 | 4.4 |
| 4 | 4.9 |

EXAMPLE 3

Binding of IgG to AvidChrom Hydrazide Gel Following Enzymatic Oxidation

Oxidation of the glycoconjugate may also readily be accomplished with an enzymatic system comprising galactose oxidase and catalase [Petkov, L. et al., Biotechnol. Techniques 4(1):25–30 (1990)]. Depending on the nature of the material to be bound, it is sometimes useful to treat the material first with neuramidase or some other suitable agent to remove sialic acid residues prior to oxidation; such pretreatment, however, is generally not necessary with most immunoglobulins.

10u of galactose oxidase and 40,000u of catalase, dissolved in 1 ml of 0.1M potassium phosphate (pH 7.0), was added to 10 mg of IgG dissolved in 1 ml of 0.1M potassium phosphate (pH 5.0). The mixture was then incubated for 1 hour at room temperature. Thereafter, 1.7–1.8 ml of the mixture was injected into a 1 ml AvidChrom Hydrazide cartridge and allowed to incubate in the cartridge for 1 hour. Unbound glycoconjugate was removed from the cartridge by sequential washing with 4–5 ml of 0.1M sodium acetate (pH 5.0) and 4–5 ml of 0.1M sodium acetate (pH 3.5). The amount of unbound glycoconjugate was estimated to be 1.9 mg. By subtraction, the amount of enzymatically oxidized IgG immobilized was at least 8.1 mg per ml of the gel. This method employing enzymatic oxidation is thus useful as an alternative gentle means of oxidizing and immobilizing glycoproteins, particularly suitable for those cases wherein the use of a chemical oxidant, such as sodium periodate, may cause damage to a particular glycoconjugate.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

We claim:

1. A method for immobilization of a glycoconjugate on a hydrazide gel resistant to oxidation by an oxidizing agent, comprising:
   preparing a solution of said glycoconjugate and said oxidizing agent which provides an oxidized glycoconjugate upon incubation;
   bringing said solution containing said glycoconjugate and oxidizing agent directly into contact with said hydrazide gel without prior removal of said oxidizing agent from said solution; and
   reacting said oxidized glycoconjugate with said hydrazide gel.

2. A method according to claim 1, wherein said glycoconjugate is a glycoprotein.

3. A method according to claim 2, wherein said glycoprotein is an immunoglobulin.

4. A method according to claim 1, wherein said hydrazide gel comprises a synthetic polymer with terminal hydrazide groups.

5. A method according to claim 4, wherein said hydrazide gel comprises a vinyl alcohol polymer composed exclusively of C, H and O atoms and containing terminal hydrazide groups.

6. A method according to claim 1, wherein said hydrazide gel comprises a silica gel with terminal hydrazide groups.

7. A method according to claim 1, wherein said oxidizing agent is a chemical oxidizing agent.

8. A method according to claim 7, wherein said chemical oxidizing agent is sodium periodate.

9. A method according to claim 1, wherein said oxidizing agent is an enzymatic oxidizing agent.

10. A method according to claim 9, wherein said enzymatic oxidizing agent comprises galactose oxidase and catalase.

11. A method according to claim 1, wherein said incubation is carried out prior to bringing said solution into contact with said gel, and said reacting is effected subsequent to said incubation.

12. A method according to claim 11, wherein said incubation is effected for about 30 minutes.

13. A method according to claim 11, wherein said reacting is effected for about 15 minutes.

14. A method according to claim 1, wherein said incubation is carried out after bringing said solution into contact with said gel.

15. A method according to claim 1, further comprising washing said gel with a buffer solution to remove unbound materials.

16. A method for preparing a cartridge comprising an oxidized glycoconjugate bound to a hydrazide gel, said method comprising:
   oxidizing a solution containing a glycoconjugate with an oxidizing agent, thereby forming said oxidized glycoconjugate; and
   injecting said solution into a cartridge containing said hydrazide gel without prior removal of said oxidizing agent.

* * * * *